United States Patent [19]

Myerholtz et al.

[11] Patent Number: 5,306,644
[45] Date of Patent: Apr. 26, 1994

[54] MASS SENSOR METHOD FOR MEASURING ANALYTES IN A SAMPLE

[75] Inventors: Carl A. Myerholtz, Cupertino; May Tom-Moy, San Carlos; Darlene J. Spira-Solomon, Portola Valley; Richard L. Baer, Los Altos; Thomas P. Doherty, San Mateo, all of Calif.

[73] Assignee: Hewlett-Packard Company, Palo Alto, Calif.

[21] Appl. No.: 41,662

[22] Filed: Apr. 1, 1993

Related U.S. Application Data

[63] Continuation-in-part of Ser. No. 792,975, Nov. 15, 1991, Pat. No. 5,283,037, which is a continuation-in-part of Ser. No. 251,149, Sep. 29, 1988, Pat. No. 5,130,257, which is a continuation-in-part of Ser. No. 876,804, Apr. 29, 1992, which is a continuation of Ser. No. 404,721, Sep. 8, 1989, abandoned, which is a continuation-in-part of Ser. No. 251,149, Sep. 29, 1988, Pat. No. 5,130,257.

[51] Int. Cl.$^5$ ............... G01N 27/00; G01N 33/00; H01L 41/00; H01L 41/08
[52] U.S. Cl. .................. 436/149; 73/61.45; 73/61.49; 310/311; 310/312; 422/68.01; 422/82.01; 436/151
[58] Field of Search ............. 73/61.45, 61.49; 310/313 R, 313 D, 312, 311; 422/68.01, 82.01; 436/149, 151

[56] References Cited

U.S. PATENT DOCUMENTS

| | | | |
|---|---|---|---|
| 4,025,954 | 5/1977 | Bert | 358/213 |
| 4,789,804 | 12/1988 | Karube et al. | 310/311 |
| 4,847,193 | 7/1989 | Richards et al. | 435/6 |
| 4,965,479 | 10/1990 | Elliot et al. | 310/313 D |
| 5,130,009 | 7/1992 | Marsoner et al. | 704/403 |
| 5,130,257 | 7/1992 | Baer et al. | 436/151 |
| 5,135,852 | 8/1992 | Ebersole et al. | 435/39 |
| 5,179,028 | 1/1993 | Vali et al. | 310/312 X |

FOREIGN PATENT DOCUMENTS

WO90/05305  5/1990  PCT Int'l Appl. .

OTHER PUBLICATIONS

Calabrese et al., "Surface Acoustic Wave Devices as Chemical Sensors in Liquids Evidence Disputing the Improtance of Rayleigh Wave Propagation", Anal. Chem, 59, 1987 833-37.
Flory et al., "Surface Transverse Wave Mode Analysis and Coupling to Meterdigital Transducers", 1987 Ultrasonics Symposium, pp. 313-318.
Lee, D. L., "A Theoretical Analysis of Surface Skimming Bulk Waves", 1978 Ultrasonics Symposium Proceedings, pp. 675-679.
Arkins, "Silane Coupling Agent Chemistry", Petrach Systems Register and Review, Anderson et al., Editors, 1987.
Nabauer, A. et al., "Biosensors Based on Piezoelectric Crystals", Sensors and Acuators, Bl, 1990, pp. 508-509.
Roederer, Joy E. et al., "Microgravimetric Immunoassay with Piezoelectric Crystals", Anal. Chem. 1983, pp. 2333-2336.
Wong, Shan S., "Chemistry of Protein Conjugation and Cross-Linking", CRC Press, Inc., Boca Raton, Fla., pp. 295-316.

*Primary Examiner*—James C. Housel
*Assistant Examiner*—Milton I. Cano

[57] ABSTRACT

A system for accurate and precise measurements of analyte(s) in a system. The measurement system comprises piezoelectric surface wave sample devices, at least one piezoelectric surface wave reference device, and the measurement instrument.

18 Claims, 5 Drawing Sheets

$M = K_\emptyset$
$V = K_\emptyset \cos(\Delta\emptyset)$
$\approx K_\emptyset \Delta\emptyset$

MASS SENSOR METHOD FOR MEASURING ANALYTES IN A SAMPLE

CROSS-REFERENCE TO RELATED APPLICATIONS

This application is a continuation-in-part of U.S. Ser. No. 07/792,975 filed Nov. 15, 1991 which, in turn, is a continuation-in-part of U.S. Ser. No. 07/251,149, filed Sep. 29, 1988 now U.S. Pat. No. 5,130,257; this application is also a continuation-in-part of U.S. Ser. No. 07/876,804 filed Apr. 29, 1992 which is a continuation of U.S. Ser. No. 07/404,721 filed Sep. 8, 1989, now abandoned which, in turn, is a continuation-in-part of U.S. Ser. No. 07/251,149, filed Sep. 29, 1988 now U.S. Pat. No. 5,130,257, the disclosures of all of which are incorporated herein by reference in their entirety.

BACKGROUND OF THE INVENTION

1. Field of the Invention

The present invention relates to analytical chemistry, and, more particularly, to devices and methods for determining the concentration of analytes in liquid samples.

2. State of the Art

In the field of analytical chemistry, there is a continuing interest in developing new, simpler and more reliable techniques to detect and measure the presence of analyte(s) in samples. In many instances, both speed and accuracy are important for the measurement, particularly with certain physiologically active compounds. In other situations, convenience can be made a major consideration.

Piezoelectric sensors have been used as microgravimetric immunoassay devices (see, for example, Joy E. Roederer and Glenn J. Bastiaans, "Microgravimetric Immunoassay with Piezoelectric Crystals", Anal. Chem. 1983, 2333–2336). These sensors operate on the principle that changes in the amount of mass attached to their surface cause shifts in the resonant frequency.

For ascertaining the concentration of a compound in a liquid, the piezoelectric sensor is preferably a surface transverse wave device or a Love wave device (collectively referred to as "piezoelectric surface wave devices"). Such devices are known in the art and are disclosed, for example, in U.S. Pat. No. 5,130,257 and U.S. patent application Ser. Nos. 07/792,975 and 07/404,721, the disclosures of which are incorporated herein by reference in their entirety.

Piezoelectric surface wave devices and other surface acoustic wave devices have come into general use, primarily for filtering radio frequency signals. A typical device is constructed on a piezoelectric substrate and has interdigital input and output transducers defined by precise electrode fingers.

In the case of piezoelectric surface wave devices, selective mass detection is achieved by coating the surface of the device with a chemically reactive layer (e.g., a receptor layer) that preferentially reacts with the substance to be detected such that the mass of the receptor layer changes in the presence of this substance. These devices function as chemical sensors that can measure the concentration of the selected class of compounds in a solution into which the sensor or device is immersed. For example, to measure the concentration of a specific antibody in a solution, a piezoelectric surface wave device is utilized in which the receptor layer contains the antigen corresponding to this antibody. The concentration of this antibody in a liquid can be measured by immersing the device in the liquid. Antibody present in the liquid will bind to the surface of the device, thereby increasing the mass loading of the top surface. Radio frequency energy coupled into the device through the input transducer is converted to a surface acoustic wave confined to within a few wavelengths of the surface. The velocity of the surface acoustic wave will vary according to the mass loading of the top surface of the device. The surface acoustic wave propagates along the surface of the device until it encounters the output transducer, which converts the surface acoustic wave back into RF energy. The change in velocity of the surface acoustic wave with the mass loading of the surface of the device translates into variation of the phase of the radio frequency signal output by the output transducer which can then be correlated to the mass of the antibody bound to the surface.

The mass sensitivity (i.e., the fractional frequency change divided by the mass change of material deposited on the surface of the device) increases as the mass of the piezoelectric surface wave device is decreased or, correspondingly, as the device thickness is decreased. A practical lower limit of about 100 microns, corresponding to a resonance frequency of about 20 MHz, is imposed on device thickness by manufacturing difficulties. Consequently, the sensitivity of piezoelectric surface wave devices is limited.

As an additional complication, while prior art devices attribute the shift in resonant frequency in piezoelectric surface wave devices used in liquid sample (e.g., aqueous solutions) to changes in the mass attached to the surface, not all of this shift is due solely to increases in the mass. In particular, physical and chemical factors such as temperature, pressure, non-specific binding, ionic strength, conductivity, mass density, viscosity, etc., are all interrelated to the shift in resonant frequency and interfere with any direct correlation between the shift in resonant frequency and the changes in mass attached to the surface of the device. While this interference can be minimized to some extent, a true correlation between frequency shifts and mass is not possible.

In the prior art, multiple measurements of multiple analytes have required a large volume of analyte to be divided into separate samples, one for each measurement. In certain medical testing applications, only a limited quantity of analyte may be available. Without the ability to perform multiple measurements of multiple analytes from a single sample, the number of measurements that may be performed is therefore limited.

SUMMARY OF THE INVENTION

A measurement system for determining the amount and/or presence of one or more analytes in a sample is provided. The measurement system employs a plurality of piezoelectric surface wave devices (e.g., STW or Love devices) which respond to the chemical environment proximal to the device surface. In particular, the measurement system employs both sample and reference piezoelectric surface wave devices. The reference device(s) provides a means to account for changes in shifts in the resonant frequency which do not correlate to mass changes on the surface of the device due to the presence of the assayed analyte(s) (e.g., interference). This interference from the data collected from the sample device can be removed mathematically so as to provide a significantly more accurate calculation of the concentration of the chemical measured by the sample device.

The present invention, generally speaking, provides an assay method which yields accurate detection of an analyte in a sample while accounting for interferences that cause shifts in the resonant frequency that do not correlate to mass changes on the surface of piezoelectric surface wave devices.

This measurement system described herein encompasses both the use of a single sample piezoelectric surface wave device measuring for single or multiple analytes or multiple sample piezoelectric surface wave devices measuring for single or multiple analytes. When multiple sample devices are employed to measure a single analyte, the measurement system described herein can provide for multiple readings on the same analyte concentration which, accordingly, provides for an accurate and precise system of measurement including a statistical analysis of the measurement results.

Methods for regenerating devices and calibrating the system are also described.

Accordingly, in one of its device aspects, the present invention is directed to a measurement system for determining the amount of one or more analytes in a liquid sample suspected of containing such analyte(s) which system comprises:

A plurality of piezoelectric surface wave sample devices comprising a receptor layer attached to the surface thereof which receptor layer contains receptor molecules which are complementary to the analyte(s) and which device generates data relating to the mass change on the surface of the device arising from contacting the device with the liquid sample;

at least one piezoelectric surface wave reference device comprising a receptor layer having little or no affinity for the analyte(s) and which generates data as to the interferences arising from contacting the device with the liquid sample; and a measurement instrument capable of correlating the data from the sample and reference devices so as to provide data on the presence and/or amount of the analyte(s) in the liquid sample.

In one of its method aspects, the present invention is directed to a method for determining the amount and/or presence of one or more analytes in a liquid sample suspected of containing such analyte(s) which method comprises:

(a) contacting the liquid sample with a measurement system for determining the amount of analyte in a liquid sample suspected of containing the analyte which comprises:

a plurality of piezoelectric surface wave sample devices comprising a receptor layer attached to the surface thereof which receptor layer contains receptor molecules which are complementary to the analyte(s) and which device generates data relating to the mass change on the surface of the device arising from contacting the device with the sample;

at least one piezoelectric surface wave reference device comprising a receptor layer having little or no affinity for said analyte(s) and which generates data as to the interference arising from contacting the device with the liquid sample; and a measurement instrument capable of correlating the data from the sample and reference devices so as to provide data on the presence and/or amount of the analyte(s) in the liquid sample;

(b) obtaining data from both the sample and reference devices; and (c) determining the presence and/or concentration of the analyte(s) in the liquid sample.

In another embodiment, this invention is directed to an economical, easy-to-use chemical analyzer capable of performing multiple measurements of multiple analytes from a single liquid sample. The chemical analyzer includes single or multiple piezoelectric surface wave sample devices for varying a characteristic of an applied radio frequency signal in accordance with particular properties of a chemical sample. The chemical analyzer also includes a piezoelectric surface wave reference device for varying the same characteristic of the radio frequency signal in accordance with extraneous influences (interference) other than the particular properties of interest of the chemical sample. To the extent that the piezoelectric surface wave reference device is sensitive to and varies the characteristic of the radio frequency signal in accordance with those particular properties, it does so only to a degree much less than the piezoelectric surface wave sample devices. A switching device applies a radio frequency signal from a single radio frequency source to both single or multiple piezoelectric surface wave sample devices and the piezoelectric surface wave reference device. A mixing device combines a radio frequency signal varied by the piezoelectric surface wave reference device with a selected radio frequency signal varied by one of the piezoelectric surface wave sample devices to produce an output signal containing information regarding at least one of the particular properties of the chemical sample.

BRIEF DESCRIPTION OF THE DRAWINGS

The present invention can be further understood with reference to the following description in conjunction with the appended drawings. In the drawings.

DETAILED DESCRIPTION OF THE INVENTION

In the following, there will be described a measurement system that provides accurate measurements of analyte(s) in samples. The measurement system utilizes piezoelectric surface transverse wave or Love Wave devices (collectively "piezoelectric surface wave devices") to measure the concentration of the target analyte(s).

A piezoelectric surface wave device generally comprises a piezoelectric substrate, one or more transducers, typically interdigital transducers (IDT), and gratings or plates which trap the mode to the surface of the substrate. A grating-based piezoelectric surface wave waveguide or device is known as an STW device, whereas a plate-based piezoelectric surface wave waveguide or device is known as a Love Wave device. Additionally, for piezoelectric surface wave sample devices, the device includes a chemically reactive layer (receptor layer) to react with the preselected analyte(s) to be detected. Such devices are disclosed in copending U.S. patent application No. 07/792,975 and U.S. patent No. 5,130,257 (issued based on the then copending U.S. patent application No. 07/251,149), both of which are herein incorporated by reference in their entirety. As such, the measurement system is capable of determining the amount and/or presence of analyte(s) in a sample, particularly a liquid sample.

In the following description of the measurement system, the term "analyte" means a compound, chemical, or composition which specifically binds to a receptor so as to allow measurement of the concentration of the analyte. An analyte may be a ligand, usually an antigen or hapten, an antibody, a single or a plurality of oligosaccharide, analytes which share at least one common epitope or determinant site such as different analytes using a common binding site such as biotin, and the like. An analyte which recognizes a particular receptor is said to be complementary to that receptor.

Also in the following description of the measurement system, the term "receptor" refers to any compound which specifically binds to an analyte so as to allow measurement of the concentration of the analyte. Receptors which recognize a particular analyte are said to be complementary to that analyte. Suitable receptors include, by way of examples, antibodies, antibody fragments, antigens, haptens, nucleic acids, particularly single stranded nucleic acids, cells, hormones, binding proteins, oligosaccharide, lectins, avidin, biotin, and the like.

A receptor and its complementary analyte are sometimes referred to as a receptor/analyte binding pair. Receptor/analyte binding pairs are well known in the art and include antigen/antibody pairs, biotin/avidin pairs, lectin/oligosaccharide pairs, single stranded nucleic acids and its complementary single stranded pair, and the like. A particularly preferred receptor/analyte pair is the antibody/antigen pair.

Further in the following description of the measurement system, the term "preselected analyte" refers to the analyte complementary to the receptor placed on the surface of the piezoelectric surface wave sample device. The term "piezoelectric surface wave sample device" or "piezoelectric surface wave chemical device" refers to a piezoelectric surface wave device which contains one or more different receptors bound directly or indirectly to its surface so as to be able to selectively bind one or more analytes complementary to the receptor(s). The receptors are typically attached to the piezoelectric surface wave sample device surface by covalent bonds but other types of linkage are possible (e.g., ionic attachment, etc.).

Methods for the attachment of receptors to such a surface are well known in the art and include, by way of example, the use of organic silanes, avidin or strepavidin, biotin, proteins, polymers, lipid bilayers, and the like. The specific means for attachment to the piezoelectric surface wave device surface are not critical and any well known means for attaching a receptor to a solid surface can be used. See, for example, Wong, "Chemistry of Protein Conjugation and Cross-Linking", CRC Press, Inc., Boca Raton, Fla., which discloses conventional means for the attachment of a protein receptor to the surface of a solid support.

In one preferred embodiment, the receptor is attached to the surface through a binding layer ("reactive surface layer") attached to the surface of the piezoelectric substrate which includes $SiO_2$ and derivatives of $SiO_2$. See, for example, U.S. patent application Ser. No. 07/404,721 which is herein incorporated by reference in its entirety. Additionally, when such a reactive surface layer is employed, it coats the surface of the piezoelectric surface wave device including gratings, plate, etc., and, accordingly, shields the surface of the device from undesirable chemical activity.

In this embodiment, the receptor layer can be coupled directly to the reactive surface layer via well known chemistry (see Wong, supra) or can be bound to a ligand binding layer which, in turn, is coupled to the reactive surface layer. In this latter embodiment, the ligand binding layer acts as a coupling layer between the device surface and the receptor layer (ligand bearing layer).

In one particular embodiment and by way of example only, the reactive surface layer is formed in a three step process which first involves the sputter deposition of $SiO_2$ (about 100 to about 1000 Angstroms thick and preferably about 500 Angstroms thick) onto the piezoelectric surface wave device surface which results in a number of reactive hydroxyl groups on the surface. In the second step, the hydroxyl groups are then treated with an organosilane coupling agent to further functionalize the reactive surface layer.

In this regard, the organosilane coupling agent is preferably represented by the formula $R_nSiX_{(4-n)}$ where X represents a hydrolyzable group, for example, alkoxy, acyloxy, amine, chlorine and the like; R represents a non-hydrolyzable organic radical that possesses functionality which enables the coupling agent to bond with organic resins and polymers, and the like; and n is an integer equal to 1, 2 or 3. One example of such an organosilane coupling agent is 3-glycidoxypropyltrimethoxysilane (GOPS) and the chemistry for this step is well known in the art. See, for example, Arkins, "Silane Coupling Agent Chemistry", Petrach Systems Register and Review, Anderson et al. Editors, (1987). Another example of an organosilane coupling agent is (γ-aminopropyl)triethoxysilane. Other suitable coupling agents are well known in the art.

In a third step, the organosilane coupling agent (now covalently attached to the surface of the piezoelectric substrate) is bound directly or after derivatization so as to provide for reactive surface layer on the surface of the piezoelectric surface wave device. As an example of this latter embodiment, if the organosilane coupling agent contains epoxy groups, then these groups can be converted to reactive aldehyde groups by conventional methods (e.g., reaction with sodium periodate) so as to provide for a surface layer on the device which is reactive with amine groups.

The ligand binding layer is then attached by contacting the reactive surface layer with a ligand binding reagent under conditions which permit the ligand binding reagent to strongly bind to the reactive surface layer so as to form a ligand binding layer. Suitable ligand binding reagents are well known in the art and the only requirement is that the ligand binding reagent contain sufficient functionality so as to both bind to the reactive surface layer and the receptor.

Preferred ligand binding reagents including antibodies, avidin, strepavidin, lectins, etc. In one embodiment, the ligand binding reagent is avidin and the surface reactive layer contains aldehyde groups which then covalently bind to the avidin through the amine groups thereon to form imines (i.e., Schiff bases—N=C<). Reduction of the imine with a suitable reducing agent such as sodium cyanoborohydride at suitable pH provides the amine derivative and results in the covalent attachment of the avidin to the surface layer of the piezoelectric surface wave device.

Alternatively, if the reactive surface layer of the piezoelectric device contains amine functionality, then it can be directly reacted with the carboxyl groups on avidin to form covalent amide bonds therewith. In this embodiment, it may be desirable to activate the carboxyl groups of the avidin prior to reaction with the amine functionality.

In any event, after formation of the ligand binding layer, the receptor or ligand bearing layer is formed. This layer is readily formed by contacting the ligand binding layer with a receptor molecule which is selective for the preselected analyte and which contains further functionality suitable for binding to the ligand binding layer. The coupling of a receptor molecule to a ligand binding layer is well known in the art. Preferred receptor molecules include antibodies, antigens, etc. which contain amino and carboxyl functionality allowing them to be bound to the ligand binding layer with minimum loss of activity for the preselected antigen. Other preferred receptor molecules are biotinylated antibodies which become bound to the preferred avidin ligand binding layer by tight biotin/avidin bonds and which are nevertheless selective for the preselected analyte.

As is apparent, the same or different receptors can be bound to the surface of a piezoelectric surface wave device. When the same receptors are employed, the resulting individual device can detect both the presence and concentration of the preselected analyte. When different receptors are employed, the resulting individual device can detect only the presence of one of the preselected analytes but cannot determine which analyte(s) are present or their concentration.

Additionally, while the above discloses one method for attaching a receptor layer onto the surface of the piezoelectric surface wave device, other methods are well known in the art including, for example, direct coupling of the receptor to the surface.

The term "piezoelectric surface wave reference device" refers to a piezoelectric surface wave device whose surface has been derivatized in a manner similar to that of the sample piezoelectric surface wave sample device but which includes a receptor layer having little or no affinity for the analyte(s) complementary to the receptors found on the surface of the piezoelectric surface wave sample device. Preferably, the piezoelectric surface wave reference device possesses a binding affinity for the preselected antigen of at least $10^2$ less, more preferably at least $10^4$ less, and even more preferably at least $10^6$ less, than the binding affinity of the piezoelectric surface wave sample device for this antigen.

Receptors having little or no affinity for an analyte are well known in the art and can be readily obtained by a variety of mechanisms including use of a protein which is not complementary to the preselected antigen. Similarly, chemically altering a nucleic acid strand so that it can no longer bind to its complementary strand is readily achieved by standard chemical procedures. Likewise, the active sites on hormones or other receptors can be chemically altered so as to be unable to bind to its complementary analyte.

Piezoelectric surface wave reference devices containing receptor layers having little or no affinity for the preselected analyte(s) are effective in reducing physical (temperature, pressure) and chemical (non-specific binding, ionic strength/conductivity/mass density and viscosity) interferences in analyte concentration determinations made by the sample devices by accounting for the shift in resonant frequency not attributable to changes in mass on the surface on the piezoelectric surface wave device.

Measurement System

In one aspect, this invention is directed to a measurement system comprising a plurality of piezoelectric surface wave sample devices, at least one piezoelectric surface wave reference device, and the measurement instrument. The piezoelectric surface wave devices include a piezoelectric substrate, interdigital transducers and a grating or plate which traps the acoustic mode at the surface of the substrate. As indicated earlier, a detailed description of such devices is set forth in U.S. patent application Ser. Nos. 07/251,149 (now U.S. Pat. No. 5,130,257) and 07/792,975, whose disclosures are herein incorporated by reference.

Also, as previously indicated, the presence and/or amount of the preselected analyte(s) in a sample is provided by the mass change on the piezoelectric surface wave sample devices which takes the form of a shift in the resonant frequency (or other related parameters such as phase delay). The measurement instrument described herein provides a means for data acquisition to measure the shift in the resonant frequency or the phase delay from both the piezoelectric surface wave sample devices and reference device(s).

The measurement system described herein may be single or multi-channel. A single channel measurement system comprises piezoelectric surface wave sample device(s) together with the reference device in series on the same substrate (e.g., FIG. 6B). An example of a multi-channel measurement system is illustrated, for example, in FIG. 4A.

Alternatively, a preferred two channel measurement configuration would mix the piezoelectric surface wave sample devices and reference device output signals before amplification. Liquids would flow in parallel over the sample and reference devices in order to synchronize their exposure cycles and reduce any sampling interferences. Thus, in this configuration, explicit reference correction would no longer be required. A hybrid device containing both sensing and reference device capability may be utilized.

The system also provides means for evaluating and calibrating the response of the piezoelectric surface wave sample devices to non-specific effects. For example, the system can be checked and calibrated with a solution of known viscosity and known conductivity. Such a solution should generate a predicted signal response and range of acceptable signal responses. Thus, when the sample devices are exposed to such a solution, the condition of the fluid path and dynamics prior to sample introduction are determined.

Once the stability of the system to a solution which does not contain the target analyte is assessed, an assortment of sample solutions, standard solutions, or solutions with internal standards may be introduced. Standard procedures are utilized to introduce the samples to the piezoelectric surface wave sample and reference devices. The samples may be directly introduced to the sample devices, or alternatively, the samples may be augmented with appropriate competing receptor binding members if the detection of the analyte is based on competition of the analyte for binding to the receptor. Such competition is desirable when detecting relatively low molecular weight analytes.

As discussed below, the measurement system also provides a means for measuring the phase delay or a related parameter such as frequency of the piezoelectric surface wave sample and reference devices. The multiplexed electronics, described below, include a means for launching acoustic waves through each device, a means for phase adjustment, mixing and amplification. The system furthermore provides a means for data acquisition software. Signal processing to account for the piezoelectric surface wave reference device response may be performed in a manner that will become readily apparent from the following description.

Standard/conventional means can be employed to introduce liquid samples to the piezoelectric surface wave sample and reference devices as well as for defining sample volume. In some configurations, this may include a fluidic system to direct reagent flow and a means for varying the rate at which sample contacts the sample and reference devices, where the actual measurement may be static or dynamic. The instrument permits a flow cassette as well as a means for sealing the cassette to the sample and reference devices. Therefore, the system can measure the relative phase delay or the rate of change of this phase delay to determine the concentration of analyte(s) in the sample.

The piezoelectric surface wave sample devices may be utilized once, used repeatedly, or used repeatedly with periodic refreshment. By periodic refreshment, it is intended that the sample device be regenerated such that it is capable of regaining functional response to the analyte.

Calibration of the system will vary depending on whether the piezoelectric surface wave sample device is to be used only once or repeatedly. If the sample device is utilized once, the calibration for that device is based on another device that is equivalent. This variation allows the sample device to perform at peak sensitivity. However, the cost per analysis is at least as great as the cost of each sample device. Thus, this approach is most useful when sample device cost is not a key concern and when inter-sample device repeatability is relatively high.

In some situations, the reuse of the piezoelectric surface wave sample device will be advantageous. In this manner, the cumulative response to a given analyte or set of analytes can be measured. While any saturation of receptors during the previous exposures may compromise accuracy, the cost per sample is reduced. This approach is most effective when the surface loading of previous samples is relatively low, as is the case for samples having low receptor binding concentrations or short exposure time. Numerous measurement cycles for a single sample device are possible with minimal loss of accuracy.

The piezoelectric surface wave sample device can also be refreshed or regenerated after each measurement to essentially regain the original response. In this variation, accuracy is improved because it is now possible to calibrate the same sample device which is used for the sample analysis. This approach also enables measurement of multiple samples by each sample device with less loss of performance than for cumulative sampling. Thus, this system provides a means for regenerating the system by dissociating the analyte, which has previously bound to the surface of the piezoelectric surface wave sample device.

Analytes may be dissociated by a variety of methods including the introduction of chemicals, such as hydrogen ions, hydroxide ions, inorganic salts, organic salts, proteolytic enzymes, proteins, denaturants, etc.; dielectric changes; the application of energy in forms such as heat, light, ultrasound, or voltage; or, any combinations of the above. The measurement system also allows for controlling and optimizing exposure parameters such as exposure time, flow rate, wash, and if employed, the energy intensity.

As indicated above, the piezoelectric surface wave sample devices utilized in the measurement system are calibrated. In the case where a sample device is used only once, calibration will occur on separate sample (calibration) devices. Where the sample devices are to be used more than once, as in the cumulative response mode, the measurement system allows the user to expose the piezoelectric surface wave sample device to one or more standard solutions sufficient to provide the desired accuracy. It is noted that the response to the standard solutions can reduce the sensitivity and performance life time of the device. Therefore, the total number of standards in sample solutions analyzed is limited in this approach.

Where the piezoelectric surface wave devices are regenerated, calibration can occur directly on the sample device. This system provides a user with the means of exposing the calibration or sample devices to the number of standard solutions sufficient to provide the desired accuracy. As the sample device can be refreshed after exposure to each standard solution, the user is not limited in the selection of either the concentration range or number of standard solutions. The data would be stored for subsequent sample analysis. An example approach of regeneration is to expose the sample device to one or multiple standard $(STD)_n$, and/or regenerations (R) between each exposure $(STD_1/R, STD_2/R, STD_3/R \ldots STD_n/R)$, then run a desired number of samples $(S_n)$, $(S_1/R, S_2/R, S_3/R, \ldots S_n/R)$, intermittently check calibration, $(STD_n/R) STD_{(n+1)}/R \ldots )$, run a desired number of samples, etc. The system also provides for calibration methods such as standard additions and other analytical techniques routinely used to reduce non-specific effects and improve accuracy.

Figure 1:
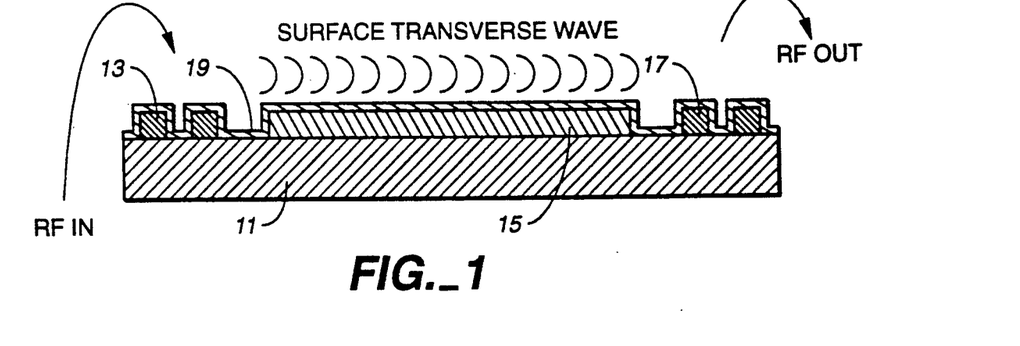
FIG. 1 is a diagram of a piezoelectric surface wave sample device.

A particularly preferred measurement instrument for use in this invention is described in FIGS. 1–6 attached. Specifically, FIG. 1 shows a piezoelectric surface wave device (Love Wave device) that may be used in the present chemical analyzer as either a sample or reference device. The device is composed of a piezoelectric substrate 11, an input transducer 13, a surface wave plate 15, and an output transducer 17. The input transducer, the surface wave plate and the output transducer are all coated with a chemical binding layer 19 described above. Briefly, when the piezoelectric surface wave sample device is immersed in a liquid sample containing chemicals in a particular class of interest, such chemicals bind to the surface of the device, thereby increasing the mass loading of the top surface. Radio frequency energy coupled into the device through the input transducer is converted to a surface acoustic wave confined to within a few wavelengths of the surface, the velocity of the surface acoustic wave varying according to the mass loading of the top surface of the device. The surface acoustic wave propagates along the surface of the device until it encounters the output transducer, which converts the surface acoustic wave back into RF energy. The change in velocity of the surface acoustic wave with the mass loading of the surface of the device translates into variation of the phase of the radio frequency signal output by the output transducer.

Figure 2:
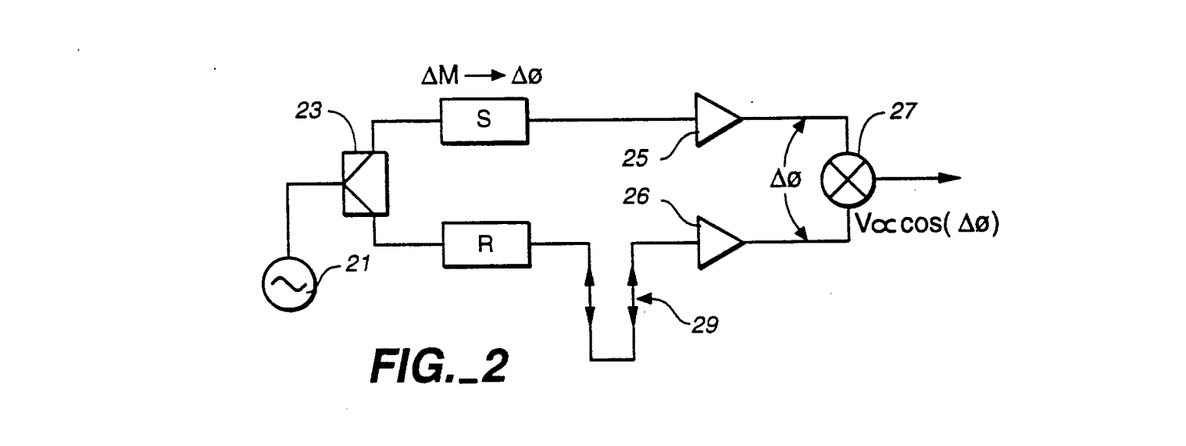
FIG. 2 is an electrical block diagram of a chemical analyzer having a single piezoelectric surface wave sample device and a single piezoelectric surface wave reference device.

Besides being sensitive to changes in mass, the piezoelectric surface wave device of FIG. 1 is also susceptible to extraneous influences including, for example, the viscosity of the chemical sample. In order to remove such extraneous influences from the final measurement, the chemical analyzer uses a piezoelectric surface wave reference device in cooperation with the sample device, both devices being subject to substantially the same extraneous influences. Referring to FIG. 2, energy from a radio frequency source 21 is split equally in a power splitter 23 and input to a sample device S and a reference device R. Both devices have the property that a change in surface mass will result in a change of phase of a signal output by the output transducer of the device. The surface chemistries of the two devices are controlled, however, such that only the sample device has a significant affinity for a particular analyte of interest. In all other respects, the devices are subject to substantially the same influences. Accordingly, the phase difference $\Delta\phi$ between the signal output by the sample device and the signal output by the reference device is directly related to the amount of analyte in the chemical sample. The signals from the devices are amplified in amplifiers 25 and 26 and input into a mixer 27. The purpose of the mixer is to produce a signal representing the phase difference between the sample device signal and the reference device signal. The mixer produces a voltage proportional to $\cos(\Delta\phi)$. An adjustable delay line 29 is provided between the output of the reference device and the input of amplifier 26 for purposes to be presently explained. In essence, the apparatus of FIG. 2 constitutes an interferometer, the sample device being placed in one arm and the reference device being placed in the other arm of the interferometer.

Figure 3:
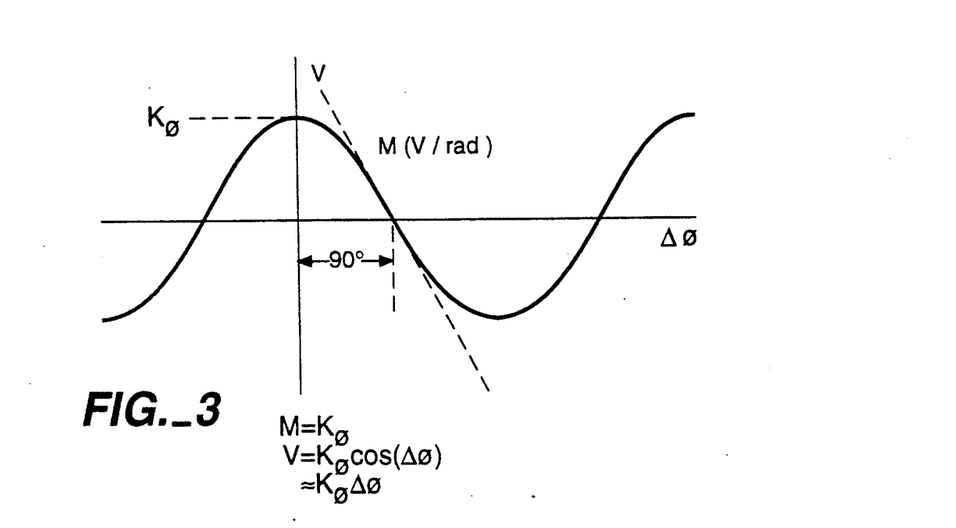
FIG. 3 is a waveform diagram of an output signal of the device of FIG. 2.

Referring to FIG. 3, the output of the mixer is a cosine wave having a maximum amplitude of $K_\phi$. At $\Delta\phi=0$, the cosine wave has a slope of 0. Operating the interferometer about this point would result in poor sensitivity. At $\Delta\phi=90°$, on the other hand, the slope M, measured in volts per radian, is of maximum magnitude. Operating the chemical analyzer about this point therefore results in maximum sensitivity. Mathematically it may be shown that $M=K_\phi$. For small excursions about the zero crossing, the relation $V=K_\phi\Delta\phi$ holds. In operation, the chemical analyzer is first calibrated by adjusting the delay line to obtain the maximum output from the mixer, the maximum output being equal to $K_\phi$. The delay line is then adjusted so as to produce a zero output from the mixer, placing signals from the sample device signal and the reference device signal in quadrature relation to one another. The chemical analyzer is then ready to perform an accurate measurement due to the high sensitivity of the chemical analyzer about the selected operating point.

In the arrangement of FIG. 2, cancellation of interferences due to influences other than the presence of analyte in the chemical sample is performed immediately and automatically by the mixer 27. Immediate and automatic cancellation is not strictly necessary, however. Furthermore, the chemical analyzer in FIG. 2 is not able to perform multiple measurements of multiple analytes from a single sample. To perform multiple measurements, the electronics of FIG. 2 may be duplicated as many times as desired. However, the resulting apparatus would be unduly complicated and expensive.

Figure 4A:
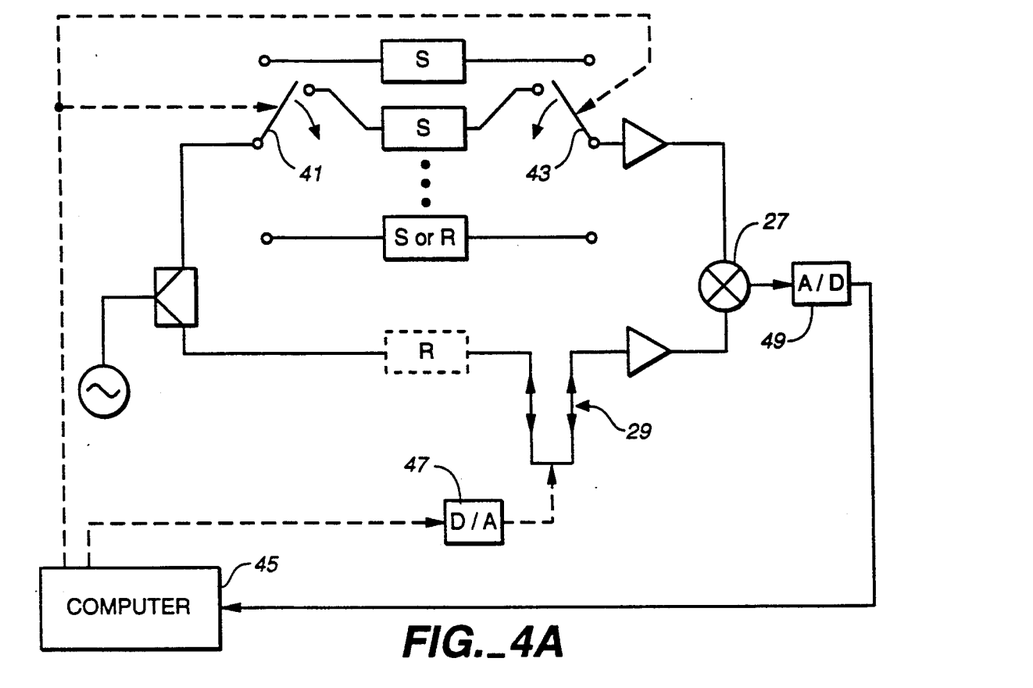
FIGS. 4A and 4B are electrical block diagrams of a chemical analyzer having a single radio frequency source, multiple piezoelectric surface wave sample devices and a single piezoelectric surface wave reference device.

Referring to FIG. 4A, using computer-controlled multiplex electronics, a chemical analyzer may be constructed that is capable of performing multiple measurements of multiple analytes from a single sample. With the reference device R located in the reference arm of the interferometer, the same basic interferometric technique may be used as in FIG. 2. Instead of a single sample device S being fixed in the sample arm of the interferometer, however, multiple sample devices are switched in and out of the sample arm using switches 41 and 43. The switches are controlled in ganged relation by a computer 45 such that both switches are connected to the same sample device S at the same time. The different sample devices each requires its own calibration setting of the variable delay line 29. Whereas the arrangement of FIG. 2 allows a mechanically variable delay line to be used, in FIG. 4A, in order for the delay to be changed in rapid synchronism with the switches, an electronically variable delay line based on varactor diodes is used. As the switches are switched, the computer retrieves the calibration value corresponding to the active device from a table of calibration values and sends the calibration value to a D/A converter 47. The D/A converter converts the calibration value to an analog value used to control the variable delay line to produce the appropriate delay for the selected device.

Figure 4B:
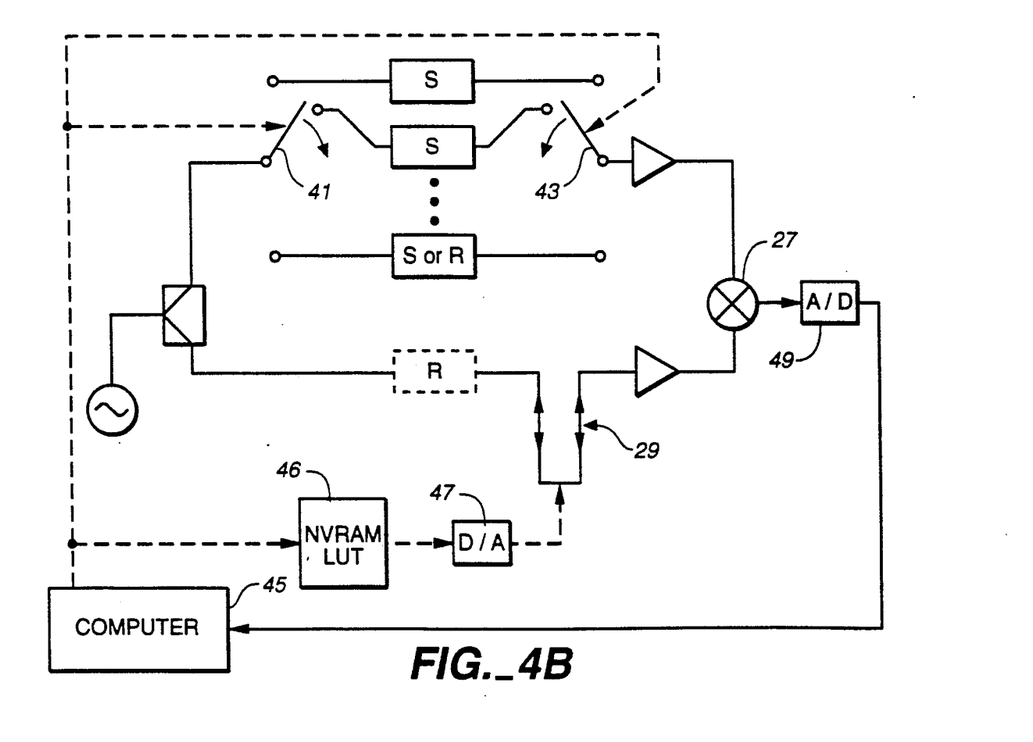

In another embodiment, shown in FIG. 4B, the table of calibration values is stored in an external look-up table 46, for example, a non-volatile RAM (NVRAM). The same signals used to control the switches may be used as an index value to the look-up table.

The reference device R, indicated in dash lines, need not remain in the reference arm of the interferometer but rather may be situated with the sample devices S on the sample side of the interferometer. Cancellation of interference is then no longer automatic and immediate but must be performed arithmetically by the computer 45. Successive outputs of the mixer 27 are converted by A/D converter 49 to digital values and stored in the computer 45 for subsequent manipulation. In particular, a reference value obtained while the reference device is connected in the device arm of the interferometer is subtracted from the values obtained with each of the other devices.

Figure 5:
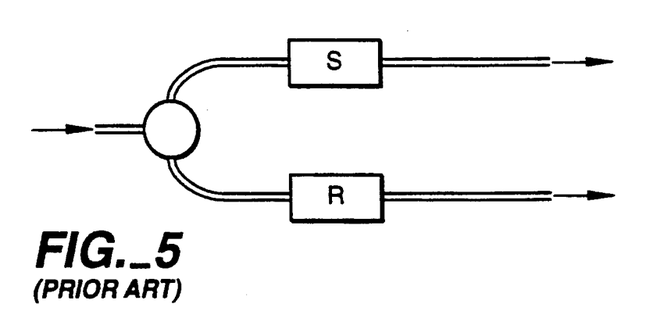
FIG. 5 is a diagram showing fluid flow in a conventional chemical analyzer.

The ability to perform interference cancellation digitally in non-real time greatly enhances the flexibility of the chemical analyzer. Referring to FIG. 5, prior art chemical analyzers have typically divided a sample flowing through the chemical analyzer into separate portions, causing one portion to flow across a sample device and another portion to flow across a reference device. In order to perform multiple measurements of multiple analytes, such an approach would require a very large sample volume. Large sample volumes are not only inconvenient but in many instances are simply not available.

Figure 6A:
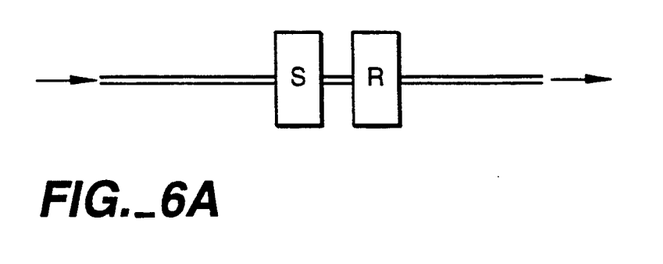
FIGS. 6A and 6B are diagrams showing fluid flow in accordance with the present invention.
Figure 6B:
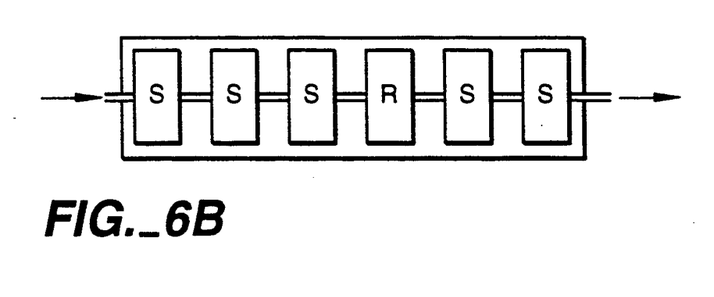

In the present chemical analyzer, multiple measurements of multiple analytes may be made from a single sample by arranging a reference device and multiple sample devices in series and causing a single sample to flow across each of the devices in turn as illustrated in FIG. 6A (single sample device S, single reference device R) and FIG. 6B (multiple samples devices S, single reference device R). Flow delay then requires that the signal from each of the sample devices and the signal from the reference device be referenced to a common time base. Assume, for example, that a first device in the series produces at an output signal time T in response to a sample flow. The sample volume then going across the first device does not reach the next device until a time $T + \Delta T_1$ where $\Delta T_1$ is the flow delay between the first and second devices. Similarly, the flow delay of each of the other devices with respect to the first device may be represented as $\Delta T_2, \Delta T_3, \ldots, \Delta T_n$. The flow delay of each of the devices with respect to the first device may be measured, for example, by producing a sudden change in the viscosity of the solution being sent through the analyzer and measuring how long it takes for that change of viscosity to be manifested at each device. These flow delays are stored in the computer 45 and used to digitally align the time-bases of signals from each of the sample devices S with the time-base of the reference device R.

Take, for example, the case of a first sample device, followed by a reference device, followed by a second sample device. The flow delay from the first sample device to the reference device may be designated as $\Delta T_1$, and the flow delay from the reference device to the second sample device may be designated as $\Delta T_2$. When the signal from the reference device is subtracted from the signal from the first sample device, the value of the reference signal at time $t + \Delta T_1$ will be subtracted from the value of the first sample device signal at time t. Similarly, when the signal from the reference device is subtracted from the signal from the second reference device, the value of the reference signal at time t will be subtracted from the value of the second sample device signal at time $t + \Delta T_2$. Each sample signal is thereby time-aligned with the reference signal despite the flow delays.

The arrangement of FIGS. 6A and 6B assumes exclusivity among the different sample devices. That is, no sample device upstream of a particular sample device is allowed to significantly affect the amount in the chemical sample of the analyte being sensed by that particular sample device.

Preferably, the devices in the arrangement of FIGS. 6A and 6B are all formed on a single piezoelectric substrate. Such a construction, besides being convenient and economical, results in all of the devices having substantially uniform characteristics. One of the devices is designated as a reference device R and coated with a chemical layer that has only minimal affinity for the analytes to be tested for but that otherwise mimics the response of the other devices.

The chemical analyzer according to the foregoing construction allows multiple measurements of multiple analytes to be taken from a single sample quickly and easily. During calibration, a buffer solution is caused to flow through the chemical analyzer and $K_\phi$ and phase setting values are obtained and stored for each of the devices. A sample to be analyzed is then caused to flow through the chemical analyzer. As the sample flows across each of the devices, separate measurements are obtained. The multiple devices may either each be used to measure a different analyte or may all be used to measure the same analyte to provide statistically greater reliability. A recycling agent may then be caused to flow through the chemical analyzer in order to refresh the devices and prepare them for a subsequent measurement. In this manner, a large amount of information may be rapidly obtained from a small amount of chemical sample.

Methodology

In its method aspects, the sample device(s) of the herein described measurement instrument is (are) contacted with a sample suspected of containing a preselected analyte so that in the presence of this analyte, the mass on the surface of the piezoelectric surface wave sample device changes. The change in the mass at the surface of the device can take the form of binding the analyte to the receptor which increases the mass of the layer. In turn, this change in mass will cause a shift in the resonant frequency (or other related parameters) of the sample device and allow for a determination of the amount of analyte in the sample.

Because of the diversity of receptors which can be attached to the surface of the piezoelectric surface wave sample device, a wide variety of measurements can be made. Furthermore, the method is capable of detecting analytes in a wide variety of environments, including fluids, gases, and colloidal suspensions.

This invention focuses, in part, on improving the accuracy and precision of measuring systems. This improvement may be accomplished by the use of at least one reference device and more than one sample device. As noted previously, such reference device and sample devices can be located on the surface of one piezoelectric substrate.

In particular, the use of a reference device permits the correlation of physical (temperature, pressure) and chemical (non-specific binding, ionic strength/conductivity/mass density and viscosity) interferences to shifts in resonant frequency not attributable to changes in mass due to the presence of the analyte on the surface of the piezoelectric surface wave sample device. In turn, this permits removing these interferences from the shifts in resonant frequency obtained on the sample devices thereby obtaining more accurate analyte information. The physical and chemical interferences from the data acquired from the sample and reference devices can be removed mathematically.

A. Analyte Measurements

Single or multiple sample devices can be used in this invention. In particular, a single sample device can be used to measure either for a single analyte (e.g., the sample device contains only one receptor which is complementary for the analyte to be detected) or multiple analytes (e.g., the sample device contains more than one receptor which is complementary for the analytes to be detected).

In the former case, the single sample device can provide a quantitative measure of the amount of analyte present. While this is the simplest measurement configuration, the breadth of the system response is reduced and there are no provisions for data redundancy.

In the latter case, the single sample device can only provide a measure of whether one or more of the preselected analytes is present in the sample tested but cannot provide a measure of the amount of any one of the analytes. Additionally, this latter configuration maximizes the breadth of the system response with no data redundancy and is best suited to screening applications where one is assaying for the presence of a group of analytes.

In this embodiment, more than one analyte/receptor binding pair are attached to the surface of the sample device and preferably, these pairs are distributed over the entire surface of the device. There are several art recognized means for controlling the distribution of these binding pairs. In one embodiment, selective chemical or physical differentiation of the immobilized surface is utilized for the sequential or heterogeneous application of specific binding members. Alternatively, co-immobilization of the chemically selective binding members can be achieved by modifying the reaction conditions to achieve the desired sensing surface area distribution and performance on the sample device.

In another embodiment, multiple sample devices, preferably formed on a single piezoelectric substrate, can be used where each device measures for a separate preselected analyte. In this embodiment, a single sample can be simultaneously screened for numerous analytes without the need for repetitive measurements.

In still another embodiment, multiple sample devices, preferably formed on a single piezoelectric substrate, can be used to measure for a single preselected analyte. When multiple sample devices are so utilized, more accurate determinations of an analyte, particularly an analyte present in minute amounts are accomplished. In this regard, it is contemplated that with multiple sample devices, the measurement system described herein would be capable of detecting less than 1 ppb of analyte in a sample. Moreover, the use of multiple equivalent sample devices to measure a given preselected analyte will improve statistical error. In the same manner, multiple related devices can be utilized which differ in affinity for a given analyte or a set of analytes. The use of this variation serves to extend dynamic range, improve resolution, as well as reduce false positives. In the embodiment of FIGS. 4A or 4B, for example, computer 45 may be used to statistically evaluate readings from the multiple sample devices.

While more than one sample device can be utilized, the measurement system described herein preferably employs no more than about 20 sample devices and no more than about 3 reference devices. More preferably, the system employs about 2 to 6 sample devices and 1 reference device.

In another embodiment, a sample device may contain different analyte/receptor binding pairs which are capable of binding the same analyte. When different analyte/receptor binding pairs for a single analyte are utilized, uncertainties in the system due to insufficient binding by a particular analyte-binding member can be minimized.

Utility

The measurement systems of the present inventions are useful for measuring a wide variety of analytes. Areas of application include, but are not limited to, environmental sensing, in vitro diagnostics, food and agriculture quality assurance and control, research, and medicine. Examples for use in environmental sensing include the determination of contaminants in natural bodies of water, the determination the quality of drinking water, determination of pesticides in a water sample, the determination of soil and sludge contamination, and to monitor industrial streams, and the like.

For in vitro diagnostics, the methods can be utilized to determine analytes in physiological fluids such as blood, plasma, saliva, cerebral spinal fluid, lymph, urine, and the like. The analytes to be detected in vitro diagnostics include immunoglobulins, and their complementary analytes, viruses (for disease diagnosis and treatment) therapeutic drugs, hormones, proteins, steroids, neurotransmittors, receptors, glycosylated proteins, carbohydrates, nucleic acids, cells, drug of abuse, cancer markers, other physiological haptens, single or double stranded nucleotide sequences, and the like. Measurement systems in food and agriculture quality control include the determination of pesticides and/or herbicides in food, dairy contaminants (antibiotics and the like), flavors, nutrients, other food components, etc. In research, the methods are useful for pharmaceutical screening, monoclonal antibody screening, the determination of immunoaffinity constants and dissociative processes, determination of relative association kinetics, nucleotide hybridization at solid phase supports, and the like. The method is also useful in veterinary and medical diagnostics.

The following experiments are offered by way of illustration and not by way of limitation.

EXPERIMENTAL

1. Silanization of Silica Wafers

EXAMPLE 1

A silanizing solution is prepared by adding one ml aminosilane to 25 ml 95% alcohol. The pH of the solution is adjusted to 4.5 with HCl. (Note: do not use acetic acid when using aminosilanes). The silane is allowed to hydrolyze 5–10 minutes. Then, the silicon wafer is added to the solution at room temperature for about 1 hour to allow binding of the silane to the wafer. The wafer is then rinsed with 95% alcohol two times, and allowed to dry under helium for 10 minutes at 50° C. in a mechanical oven.

2. Oxidation of Primary Antibody

The primary antibody is diluted in 10 mM $NaIO_4$ (in PBS buffer, pH 6.0). Dilutions of 1:10, 1:25, 1:50, 1:100 are made.

The antibody is allowed to stand for 30 minutes at 4° C. to allow oxidation of oligosaccharide in the Fc portion of the antibody.

3. Removal of $NaIO_4$ from Antibody Solution

To remove the $NaIO_4$ from the oxidized antibody solution, PD-10 columns (Pharmacia, N.J.) are utilized. The PD-10 columns are equilibrated with 25 ml of PBS pH 7.4.

To the columns 2.5 ml of sample antibody is added, and eluted with 3.5 ml of PBS buffer, pH 7.4. The antibody fraction is collected and incubated with silanized wafers at 4° C. for 1–2 hours with rocking motion.

4. Formation of Schiff's Base

To favor the formation of a Schiff base, the pH of the oxidized antibody solution is adjusted with 2 drops of 0.1N HCl using a transfer pipet. This solution is then allowed to incubate for one hour at 4° C. with rocking motion.

5. Reductive Amination of Schiff's Base to Stabilize Imine of Schiff Base

A Schiff base is formed by the reaction of an aldehyde (present on the initial Fc portion of the antibody as a result of the $NaIO_4$ oxidation) and an amine group (present on the aminosilane).

$NaCNBH_4$ is utilized to reduce and stabilize the formation of the Schiff base (amine). $NaCNBH_4$ has a rate of hydrolysis $10^{-8}$ that of $NaBH_4$. $NaCNBH_4$ is a milder reducing agent and will dissociate S—S bonds present in the antibody molecule. Therefore, the steps include:

Make a 0.1M $NaCNBH_4$ solution in PBS buffer pH 6.0.

(For a final concentration of 0.01M $NaCNBH_4$, for a 1 ml solution add 100 µl of 0.1M $NaCNBH_4$.)

The solution is mixed overnight with rotation at 4° C., followed by washing in PBS buffer, 2-3 times.

The wafers are then stored at 4° C. until use.

For monoclonal antibodies, a 1 mM $NaCNBH_3$ solution is made. The wafers are placed in microtiter plates which contain 440 µl of oxidized antibody solution, 40 µl of 1 m $NaCNBH_3$, 0.1M ethanolamine, and incubate for 15 minutes. After washing in PBS buffer, the wafers are stored at 40° C., and in a desiccator until use.

EXAMPLE 2

Measurement of Human IgG in a Sample

1. Incubation of Substrate with Avidin

The washed substrate surface as prepared in Example 1, is incubated with a solution of avidin and borate buffered saline (BBS) pH 8.5, at a concentration of about 0.1 mg/ml. The solution is mixed by gentle inversion at 4° C. for 20-24 hours.

2. Biotinylated Antibodies

Antibodies are biotinylated by mixing the antibodies with NHS-biotin in solution at a pH of 7.0. Prior to use, the avidin coated wafer is incubated with the biotinylated antibody. After bonding, the wafer surface is washed with a blocking agent, biotin, which binds to any unoccupied sites on the avidin layer. In this manner, anti-IgG antibodies are biotinylated and bound to the avidin coated devices.

These antibody coated devices were then utilized to measure the amount of IgG in samples.

Figure 7:
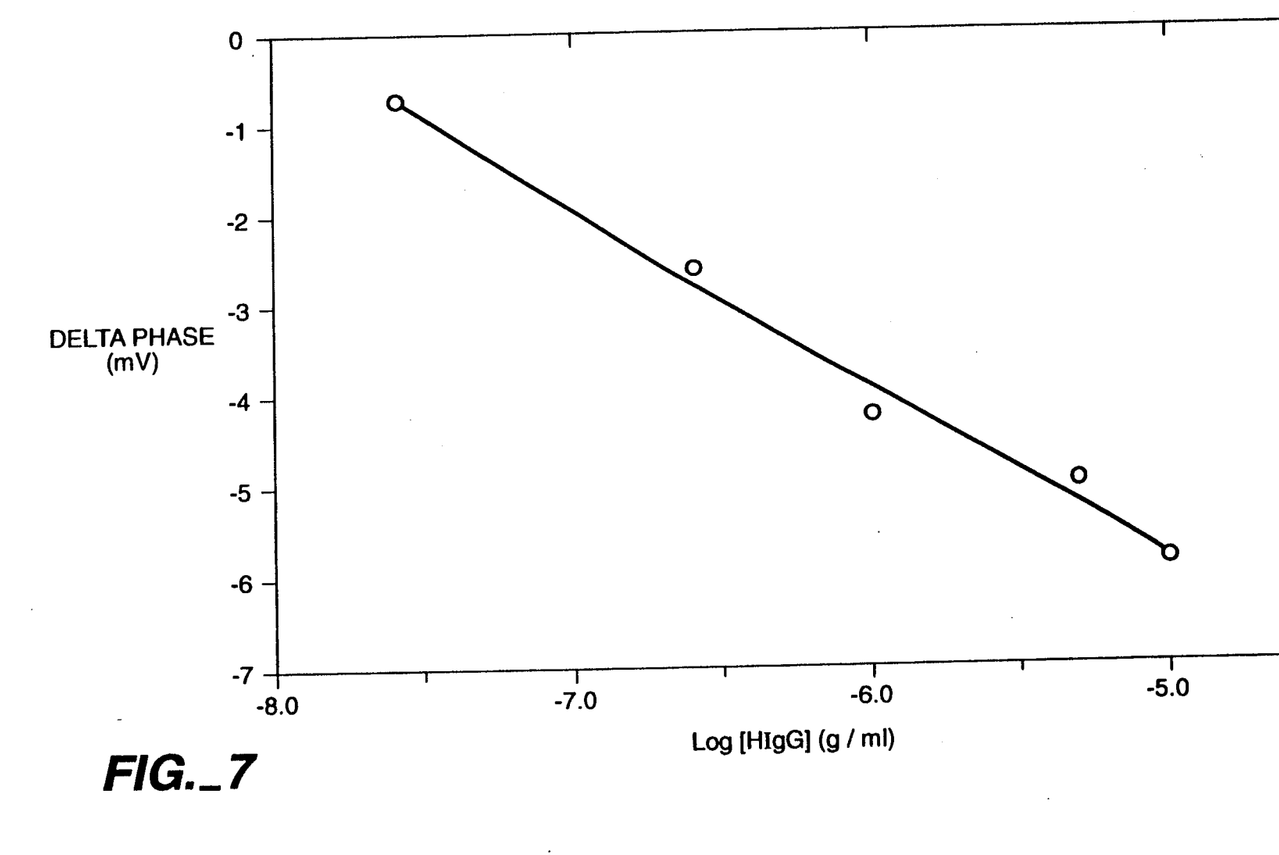
FIG. 7 depicts the dose response to Human IgG achieved using the measurement system of this invention.

Results of the measurements are given in FIG. 7.

EXAMPLE 3

Device Regeneration

Figure 8:
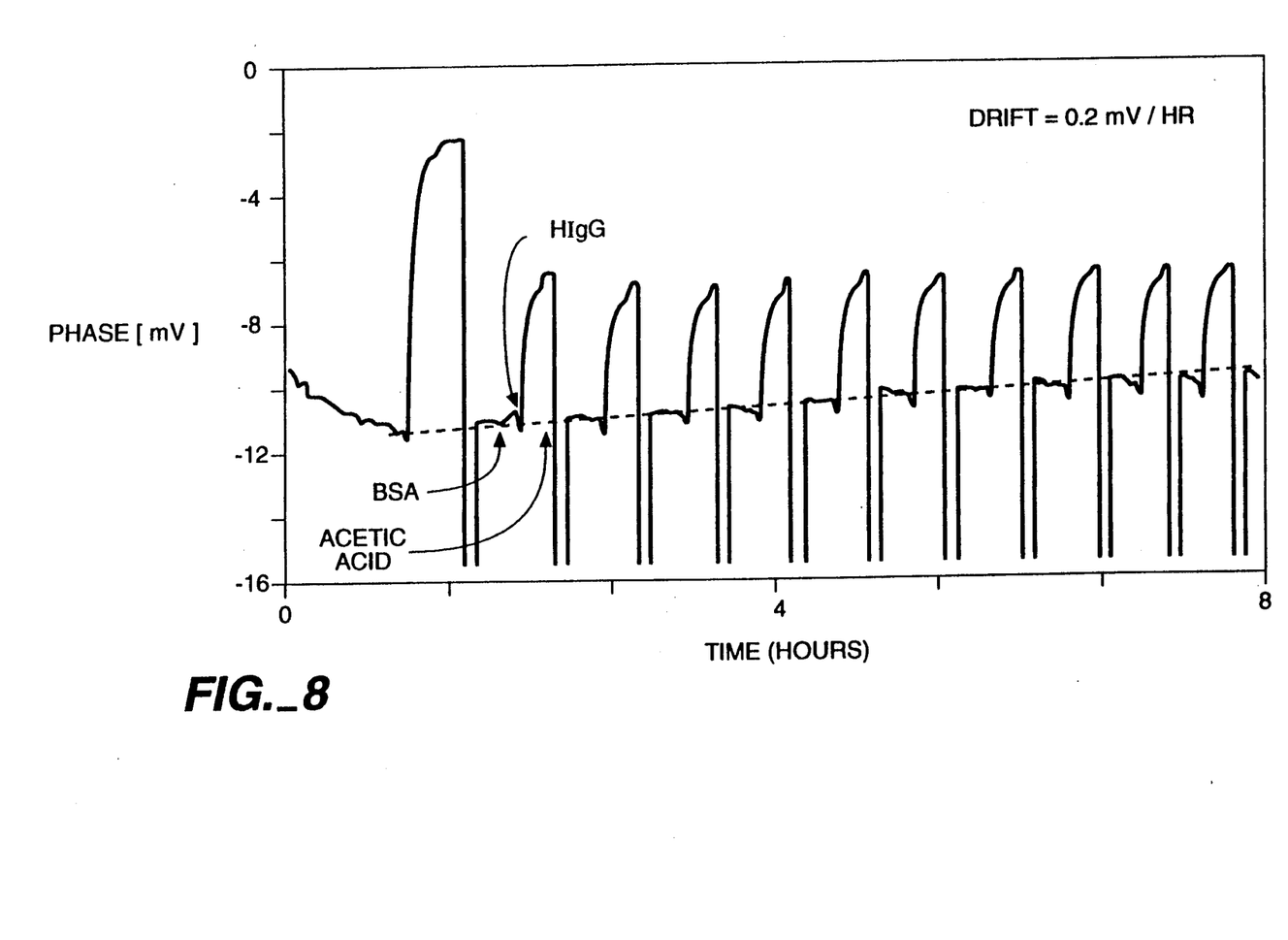
FIG. 8 depicts the piezoelectric surface wave device response after repeated recycling with acetic acid.

The devices were recycled by treatment with acetic acid. Results showing the device response and recycling performance are given in FIG. 8.

The methods of the invention have been used to measure high and low molecular weight analytes including Human IgG (See FIG. 7), sulfamethazine, amphetamine and fluorescein. The chemically selective species are covalently immobilized at concentrations of about 600 ng/cm$^2$, retain >90% of their native activity, and are stable. Over 200 regeneration cycles have been performed on a single chemical sensing device. The residual standard deviation over ten regeneration cycles (excluding the first exposure) at a fixed analyte concentration is less than 5%. The large deviation experienced in the first exposure suggests that the device should be preconditioned. The system can routinely detect less than 1 ppb of analyte and dynamic ranges exceed five orders of magnitude.

The present system provides a broadly-applicable methodology for measurement of a binding event. Any molecule of relatively high mass that can in principle bind selectively to an appropriately functionalized surface can be measured, either directly or indirectly. The invention provides precise measurements in the absence of complex or labor-intensive separation steps. Furthermore, there is no need to derivatize the sample or related reagent solutions with radioactive, fluorescent, or chemiluminescent labels.

Additional advantages of the system are that it provides high measurement performance of multiple analytes with micro-fabricated devices and electronic components that are consistent with low cost, compact instrumentation for laboratory and portable field use. The system additionally provides for referencing of physical and chemical interferences, calibration and device regeneration to improve accuracy and lower the cost per analysis.

All references cited herein are incorporated by reference. Although the foregoing refers to particular preferred embodiments, it will be understood that the present invention is not so limited. It will occur to those of ordinary skill in the art that various modifications may be made to the disclosed embodiment, and that such modifications are intended to be within the scope of the present invention.

What is claimed is:

1. A measurement system for determining the amount of at least one analyte in a liquid sample suspected of containing such analytes comprising:

a plurality of piezoelectric surface transverse wave sample devices comprising a receptor layer attached to the surface thereof, which receptor layer contains receptor molecules which are complementary to the analytes and which device generates data relating to the mass change on the surface of the device arising from contacting the device with the sample;

at least one piezoelectric surface transverse wave reference device comprising a receptor layer having little or no affinity for the analyte(s) and which generates data as to the interferences arising from contacting the device with the liquid sample; and a measurement instrument capable of correlating the data from the sample and reference devices so as to provide data on at least one of the presence and amount of the analytes in the liquid sample.

2. The system as defined in claim 1 wherein said receptor is selected from the group consisting of antibodies, antibody fragments, antigens, haptens, nucleic acids, cells, receptors, hormones, binding proteins, and oligosaccharides.

3. The system as defined in claim 2 wherein the sample and reference devices further comprise a surface layer.

4. The system as defined in claim 3 wherein the surface layer is $SiO_2$.

5. The system as defined in claim 4 wherein said surface layer further comprises a reactive surface layer bound to said surface layer wherein said reactive surface layer is derived from the group consisting of organic silanes, avidin, strepavidin, proteins, polymers, lipid layers, or synthetic coatings.

6. A method for determining at least the amount and presence of at least one analyte in a liquid sample suspected of containing such analytes comprising:
(a) contacting the liquid sample with a measurement system for determining the amount of analyte in a liquid sample suspected of containing the analyte which comprises:
a plurality of piezoelectric surface transverse wave sample devices comprising a receptor layer attached to the surface thereof which receptor layer contains receptor molecules which are complementary to the analytes and which device generates data relating to the mass change on the surface of the device arising from contacting the device with the sample;
at least one piezoelectric surface transverse wave reference device comprising a receptor layer having little or no affinity for said analytes and which generates data as to the interference arising from contacting the device with the liquid sample; and
a measurement instrument capable of correlating the data from the sample and reference devices so as to provide data on at least one of the presence and amount of the analyte in the liquid sample;
(b) obtaining data from both the sample and reference devices; and
(c) determining at least one of the presence and concentration of the analyte in the liquid sample.

7. A chemical analyzer apparatus comprising:
a plurality of piezoelectric surface transverse wave sample device means for, when in contact with a chemical sample, varying a characteristic of an applied radio-frequency signal in accordance with particular properties of said chemical sample;
piezoelectric surface transverse wave reference device means for, when in contact with said chemical sample, varying said characteristic of an applied radio-frequency signal in accordance with extraneous influences other than said particular properties of said chemical sample, and in accordance with said particular properties of said chemical sample only to a degree much less than said sample device;
means for applying a radio-frequency signal to said plurality of sample device means and to said reference device means, said means for applying including means for switching a single radio-frequency signal from one of said sample device means to another of said sample device means;
means for selecting a radio-frequency signal varied by one of said sample device means, said means for selecting including means for switching between radio-frequency signals varied by respective ones of said device means; and
means for combining a radio-frequency signal varied by said reference device means with a selected radio-frequency signal varied by said one of said sample device means to produce an output signal containing information regarding at least one of said particular properties of said chemical sample.

8. The apparatus of claim 7, wherein said means for combining comprises means for phase shifting relative to each other said radio frequency signal varied by said reference device means and said selected radio-frequency signal varied by said one of said sample device means.

9. The apparatus of claim 8, wherein said means for combining further comprises control means for controlling said means for phase shifting such that said signals are phase shifted substantially 90° relative to each other when a buffer solution is caused to contact said reference device means and said one of said sample device means.

10. The apparatus of claim 9, wherein said means for controlling said means for phase shifting comprises means for storing phase shift amounts for each of said plurality of sample device means.

11. The apparatus of claim 10, wherein said control means is further for controlling said means for applying, said means for selecting, and said means for phase shifting such that when said single radio-frequency signal is applied to a particular one of said sample device means, said means for selecting selects a radio-frequency signal varied by said particular one of said sample device means and said means for phase shifting is controlled in accordance with a phase shift amount for said particular one of said sample device means.

12. The apparatus of claim 11, wherein said means for switching included in said means for applying is for switching the single radio-frequency signal from one of said sample device means to another device from among other sample device means and said reference device means, and said means for switching included in said means for selecting is for switching between radio-frequency signals varied by respective ones of said sample device means and said reference device.

13. The apparatus of claim 12, further comprising sample flow path means for containing a flow of said chemical sample, said reference device means and a plurality of sample device means being arranged serially in a direction of flow along said flow path means.

14. The apparatus of claim 13, wherein said means for controlling is further for causing both of said switching means to switch in unison in accordance with flow delays between respective ones of said devices and a first device in said flow direction.

15. A chemical analyzer comprising:
piezoelectric surface transverse wave sample device means for, when in contact with a chemical sample, varying a characteristic of an applied radio-frequency signal in accordance with a particular property of said chemical sample;
piezoelectric surface transverse wave reference device means for, when in contact with said chemical sample, varying said characteristic of an applied radio-frequency signal in accordance with extraneous influences other than said particular properties of said chemical sample, and in accordance with said particular properties of said chemical sample only to a degree much less than said sample device;
means for applying a radio-frequency signal to said sample device means and to said reference device means, said means for applying including means for switching a single radio-frequency signal from said sample device means to said reference device means;
means for selecting a radio-frequency signal varied by one of said sample device means and said reference device means, said means for selecting including means for switching between radio-frequency signals varied by respective ones of said sample device means and said reference device means; and means for combining a radio-frequency signal varied by said reference device means with a selected radio-frequency signal varied by said one of said sample device means to produce an output signal containing information regarding said particular property of said chemical sample; and a single fluid flow path through which a fluid sample flows across one of said sample device means and said reference device means and then across another of said sample device means and said reference device means.

16. A chemical sensor for testing for a plurality of analytes in a fluid sample, comprising:

a piezoelectric substrate; and a plurality of piezoelectric surface transverse wave sample devices formed on said piezoelectric substrate, each of said piezoelectric surface wave sample devices having a different receptor layer attached to a surface thereof, each receptor layer containing receptor molecules complementary to a different one of said plurality of analytes.

17. A measurement system for testing for an analyte in a liquid sample, comprising:

a plurality of piezoelectric surface transverse wave sample devices each having a receptor layer attached to the surface thereof, each receptor layer containing receptor molecules which are complementary to the same analyte, each device generating data relating to the mass change on the surface of the device arising from contacting the device with the sample;

at least one piezoelectric surface transverse wave reference device comprising a receptor layer having little or no affinity for the analyte and which generates data as to the interferences arising from contacting the device with the liquid sample; and a measurement instrument capable of correlating the data from the sample and reference devices and statistically evaluating data from said plurality of piezoelectric surface wave sample devices so as to provide data on at least the presence and amount of the analyte in the liquid sample.

18. The system of claim 17 wherein said plurality of piezoelectric surface wave sample devices are formed on a single piezoelectric substrate.

* * * * *

UNITED STATES PATENT AND TRADEMARK OFFICE
CERTIFICATE OF CORRECTION

PATENT NO. : 5,306,644
DATED : 26 April 1994
INVENTOR(S) : Carl A. Myerholtz et al.

It is certified that error appears in the above-indentified patent and that said Letters Patent is hereby corrected as shown below:

Column 7, line 12, "bases-N=C" should read -- bases -- -N=C --.

Signed and Sealed this

Twenty-seventh Day of September, 1994

Attest:

BRUCE LEHMAN

Attesting Officer      Commissioner of Patents and Trademarks